(12) United States Patent
Van Dam et al.

(10) Patent No.: US 6,671,549 B2
(45) Date of Patent: Dec. 30, 2003

(54) PACEMAKER UTILIZING QT DYNAMICS TO DIAGNOSE HEART FAILURE

(75) Inventors: Peter M. Van Dam, Doesburg (NL); Diederick M. Keizer, Elst (NL); Mattias Rouw Rouw, Arnhem (NL); Jos P. A. Smit, Arnhem (NL)

(73) Assignee: Medtronic, Inc., Minneapolis, MN (US)

( * ) Notice: Subject to any disclaimer, the term of this patent is extended or adjusted under 35 U.S.C. 154(b) by 41 days.

(21) Appl. No.: 09/987,796

(22) Filed: Nov. 16, 2001

(65) Prior Publication Data

US 2003/0100928 A1 May 29, 2003

(51) Int. Cl.$^7$ .................................................. A61N 1/37
(52) U.S. Cl. .......................................... 607/25; 600/510
(58) Field of Search ............................. 607/25, 26, 18; 600/516, 519, 510

(56) References Cited

U.S. PATENT DOCUMENTS

| | | | |
|---|---|---|---|
| 4,316,472 A | 2/1982 | Mirowski et al. | |
| 4,375,817 A | 3/1983 | Engle et al. | |
| 4,379,459 A | 4/1983 | Stein | |
| 4,384,585 A | 5/1983 | Zipes | |
| 4,476,868 A | 10/1984 | Thompson et al. | |
| 4,556,063 A | 12/1985 | Thompson et al. | |
| 4,577,633 A | 3/1986 | Berkovits et al. | |
| 4,587,970 A | 5/1986 | Holley et al. | |
| 4,727,877 A | 3/1988 | Kallok | |
| 4,800,883 A | 1/1989 | Winstrom | |
| 4,821,723 A | 4/1989 | Baker et al. | |
| 4,830,006 A | 5/1989 | Haluska et al. | |
| 4,880,005 A | 11/1989 | Pless et al. | |

(List continued on next page.)

OTHER PUBLICATIONS

International Search Report, PCT/US02/36272(Apr. 23, 2003).

"Onset and Stability for Ventricular Tachyarrhythmia Detection in an Implantable Pacer–Cardioverter–Defibrillator" Olson et al., Computers in Cardiology, Oct. 7–10, 1986, IEEE Computer Society Press, pp 167–170.

"Automatic Tachycardia Recognition" Arzbachaecher et al., PACE, May–Jun. 1984, pp 541–547.

"Prologation of the QT Inverval at Low Heart Rate, Although Not at High Heart Rate" Davey, Barlow and Hart, Clin. Sci. (Colch), May 2000.

*Primary Examiner*—Scott M. Getzow
(74) *Attorney, Agent, or Firm*—Girma Wolde-Michael

(57) ABSTRACT

The invention presents a medical device system and method for determining the degree of heart failure of a patient, utilizing information representative of dynamic variations in patient QT, or segments of QT, over time. The dynamic variations in QT that are measured relate to characteristics of the variation of QT with rate when rate is increasing and when it is decreasing. The dynamic variations include QT dynamic range, QT hysteresis, and QT directrix, each providing important information relating to the patient's variation of QT with heart rate, or QT(RR). QT and dynamic variations of QT can be measured in both left and right ventricles, and taken over the patient's normal rate range. The dynamic data is measured and stored periodically and compared with historical data to determine progression toward heart failure. In another embodiment, the QRST signals are divided into segments, namely QRS width; ST segment; and T wave width, and variations of these segments are analyzed to provide additional information indicative of the patient's heart condition. Preferably the system utilizes a microprocessor programmed to carry out an algorithm that weighs detected variations in QT, QT segments and/or QT dynamic parameters with time to track cardiac changes.

42 Claims, 11 Drawing Sheets

U.S. PATENT DOCUMENTS

| | | |
|---|---|---|
| 4,949,719 A | 8/1990 | Pless et al. |
| 4,953,551 A | 9/1990 | Mehra et al. |
| 5,099,838 A | 3/1992 | Brady |
| 5,117,824 A | 6/1992 | Keimel et al. |
| 5,131,388 A | 7/1992 | Pless |
| 5,144,949 A | 9/1992 | Olson |
| 5,158,078 A | 10/1992 | Bennet et al. |
| 5,163,427 A | 11/1992 | Keimel |
| 5,188,105 A | 2/1993 | Keimel |
| 5,199,428 A | 4/1993 | Obel et al. |
| 5,207,218 A | 5/1993 | Carpentier et al. |
| 5,269,298 A | 12/1993 | Adams et al. |
| 5,312,453 A | 5/1994 | Shelton et al. |
| 5,314,430 A | 5/1994 | Bardy |
| 5,330,507 A | 7/1994 | Schwartz |
| 5,331,966 A | 7/1994 | Bennet et al. |
| 5,354,316 A | 10/1994 | Keimel |
| 5,511,553 A | 4/1996 | Segalowiz |
| 5,545,186 A | 8/1996 | Olson |
| 5,690,686 A | 11/1997 | Min et al. |
| 5,749,900 A | 5/1998 | Schroeppel et al. |
| 5,792,197 A | 8/1998 | Nappholz |
| 6,029,087 A | 2/2000 | Wohlgemuth |
| 6,035,233 A | 3/2000 | Schroeppel et al. |
| 6,070,100 A | 5/2000 | Bakels et al. |
| 6,071,101 A | 6/2000 | Ni et al. |
| 6,129,744 A * | 10/2000 | Boute ................... 607/25 |
| 6,219,579 B1 | 4/2001 | Bakels et al. |
| 6,456,880 B1 * | 9/2002 | Park et al. ............. 607/25 |

* cited by examiner

PACEMAKER UTILIZING QT DYNAMICS TO DIAGNOSE HEART FAILURE

FIELD OF THE INVENTION

This invention lies in the field of cardiac device systems and methods and, in particular, implantable systems that have the capacity to acquire data from the patient's heart and to process such data to provide information concerning the patient's heart. More specifically, this invention is directed toward providing an indication of degree of patient heart failure based on information derived from heart signals.

BACKGROUND OF THE INVENTION

The utilization of pacemakers for diagnostic functions as well as pacing and cardioversion therapy has increased along with the capacity of pacemaker devices to collect and store data. Several generations of pacing systems have incorporated schemes for collecting and storing data derived from the patient's heart, as well as data representative of the history of pacemaker functions. This data can be organized to provide an historical picture of the patient's heart, coded, and downloaded to an external device for analysis by a physician. For example, the physician can be provided with cardiac rate histories, instances of ectopic beats, tachycardia episodes, and the like.

More recently, increased attention has been paid to the area of heart failure (alternatively referred to simply as "HF") and mechanisms for detecting and treating this condition. As with many other diseases, early detection can provide increased opportunities for inhibiting onset and/or for effective treatment. The advent of bi-ventricular pacing systems has provided increased opportunities for treating at least some forms of heart failure. However, initiation of any form of treatment depends upon the availability of accurate information concerning the condition of the patient's heart.

One recognized indicator of heart failure is prolongation of the QT interval (or, simply, "QT"), particularly at low rates associated with rest. It is known that QT interval increases with lower rates and decreases with higher rates. This is because QT has a component that increases directly with the cardiac interval, as well as a stress dependent variation due to the autonomic nervous system. Prolongation, as the term is used here, refers not to the normal increase in QT at lower rates, but to an increase beyond the normal that is found to occur in cases of established heart failure. The literature recognizes that patients with heart failure are characterized with prolongation of the QT interval at low heart rates, although not at high heart rates. "Prolongation of the QT interval in heart failure occurs at low but not at high heart rates." Davey, Barlow and Hart, Clin. Sci (Colch) May 2000; 98(5): 603–10. The disclosed investigations found that QTc (corrected QT) intervals at rest were significantly longer in heart failure patients, and were associated principally with impairment of left ventricular systolic function.

The use of variations in QT interval or of corrected QTc as an indicator of heart failure has limitations, as stated in the above referenced publication. Although prolongation of QT interval at rest seems to be an excellent indicator of established heart failure, changes in QT by itself have not been shown to provide a reliable prognosis for the patient who is proceeding toward heart failure. What is needed is more information, collected over time, to suggest changes that can be used by the physician, or compared automatically to benchmarks, to more reliably point to onset of heart failure.

U.S. Pat. No. 5,792,197, Nappholz, discloses an implantable rate responsive pacemaker that uses a physiological demand parameter to determine a classification of the degree of patient heart failure. In the illustrated embodiment, minute volume is monitored and used as a physiological demand parameter. Variations of the parameter corresponding to different levels of activity are obtained, and differences in the parameter over time are used to determine the degree of heart failure. QT interval and cardiac contractibility are mentioned as possible parameters. However, the patent reference does not indicate specifically how to utilize QT information, nor does it suggest the range of possibilities for obtaining predictive information from QT variations. Other patents, as listed in Table 1 below, deal with the subject of identifying cardiac events and trying to determine the patient's cardiac condition, but do not optimize the information available from sensed heart signals. Accordingly, there has remained a need to more fully utilize information inherent in QT variations and to utilize that information for prognosis of heart failure.

TABLE 1

| U.S. Pat. No. | Inventor(s) | Issue Date |
| --- | --- | --- |
| 5,511,553 | Segalowitz | April 30, 1996 |
| 5,749,900 | Schroeppel et al. | May 12, 1998 |
| 5,792,197 | Nappholz | Aug. 11, 1998 |
| 6,029,087 | Wohlgemuth | Feb. 22, 2000 |
| 6,035,233 | Schroeppel et al. | March 7, 2000 |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the teachings of the resent invention.

SUMMARY OF THE INVENTION

This invention addresses the detection and progression of heart failure (HF), and particularly the detection of HF at an early enough stage to enable treatment of the patient with drugs or, in some cases, pacing therapies. The ability to accurately predict or recognize HF at an early stage may, in many cases, enable management of the condition in order to slow down its progression, and prolong a good quality of life.

It is an object of this invention to provide an implantable medical device, and a method of treatment using such device, that optimally utilizes the information inherent in patient cardiac signals to monitor onset of and progression toward heart failure, and to provide predictive indications of heart failure. It is a specific object to utilize dynamic variations of QT interval data, obtained from sensed and also paced cardiac signals. The data is utilized to predict heart failure and to provide indications of current patient degree of heart failure. The dynamic variations are referred to as dynamic QT parameters, and represent variations of QT with rate, i.e., QT(RR), that are measured as patient heart rate is first raised and then lowered. Such dynamic variations provide information indicative of HF that is not available solely from measurement of long term changes of QT at rest.

It is another object of this invention to provide an implantable medical device system and method of treatment wherein QT data is obtained from both right and left ventricles, and stored over time. The QT data from both ventricles provides an important comparison for analysis of patient cardiac condition, particularly the onset of HF.

In accord with the above objective, there is provided a system and method that incorporates an implantable medical device, and that obtains comprehensive data from patient cardiac signals, and in particular the QRS-T portions of the signals. The system analyzes the data and provides current and prognostic indications the patient's cardiac condition. The system and treatment method of this invention utilize not only QT interval data, but also make available data relating to different portions, or segments of the QT complex, i.e., the QRS width, the ST segment, and the T wave width. Each of these segments varies with time and exercise, and in some patients may contain useful prognostic data that is not obtainable just from a measurement of QT interval. As used herein, QT data refers to the QT interval, or QTc, as well as the segment data. In addition, the system and method of this invention are designed to obtain and use dynamic QT data over a range of patient heart rates, so as to capture additional information that is not available simply from the measurement of QT interval changes at rest.

In one embodiment of the invention, the dynamic rate range of QT interval is obtained by determining variation of patient heart rate with respect to one or more predetermined QT intervals as the patient exercises to raise rate and then rests, permitting rate to recover toward a rest rate. The difference between the rate found at a given QT interval as the patient heart rate rises in response to exercise, and the rate found as the patient recovers toward rest, represents a rate range that will vary in patients who are progressing toward a higher degree of heart failure. The system obtains and stores such dynamic rate range data, and provides it for indication of degree of patient heart failure.

In another embodiment of the invention, one which is a complement of rate range, dynamic QT hysteresis is measured and utilized for determination of the patient's cardiac status. In this embodiment, the patient is taken through a cycle of exercise and recovery, and QT interval is measured at one or more predetermined heart rates as rate rises in response to exercise, and again at the same rate (or rates) after the patient stops exercise and recovers. In this situation, QT interval is found to be higher as rate climbs in response to exercise than it is at the same rate as the patient recovers. This difference, or QT hysteresis, varies with time for a patient, and thus is a dynamic variable that, like the dynamic rate range, provides useful data concerning changes in the patient's cardiac condition. Dynamic QT hysteresis measurements may utilize the entire QT interval, or any combination of the segments of the QRS-T signal.

In yet another embodiment of the invention, dynamic QT directrix data is obtained that represents differences in the slope of the QT (RR) curve around a given rate during exercise and recovery. Thus, as the patient heart rate increases due to exercise, a measure of QT slope around one or more trigger rates is determined, and after cessation of exercise and recovery of rate toward rest, the slope is again determined around the same rate or rates. This slope information, like the rate range and QT hysteresis values, is dynamic with time for a patient who is advancing to greater degrees of heart failure, and thus provides further useful data to inform as to the patient's progression.

By incorporation of one or more of the above features, the system and method of this invention provide an enhanced capability for acquiring and analyzing data from which a patient's progression toward heart failure can be tracked. The system of this invention is preferably embodied with a microprocessor-based implantable device, and utilizes DSP technology to provide signal data in useful form for analysis. The system advantageously discriminates against ectopic beats that would interfere with provision of desired data, and also provides for accurate separation of the QRS-T segment data, for indicator use. In another embodiment, an analysis algorithm may use just the QRS-T data for providing indications of degree of heart failure, or may utilize such QRS-T data in combination with the dynamic data.

DETAILED DESCRIPTION OF THE PREFERRED EMBODIMENTS

Figure 1:
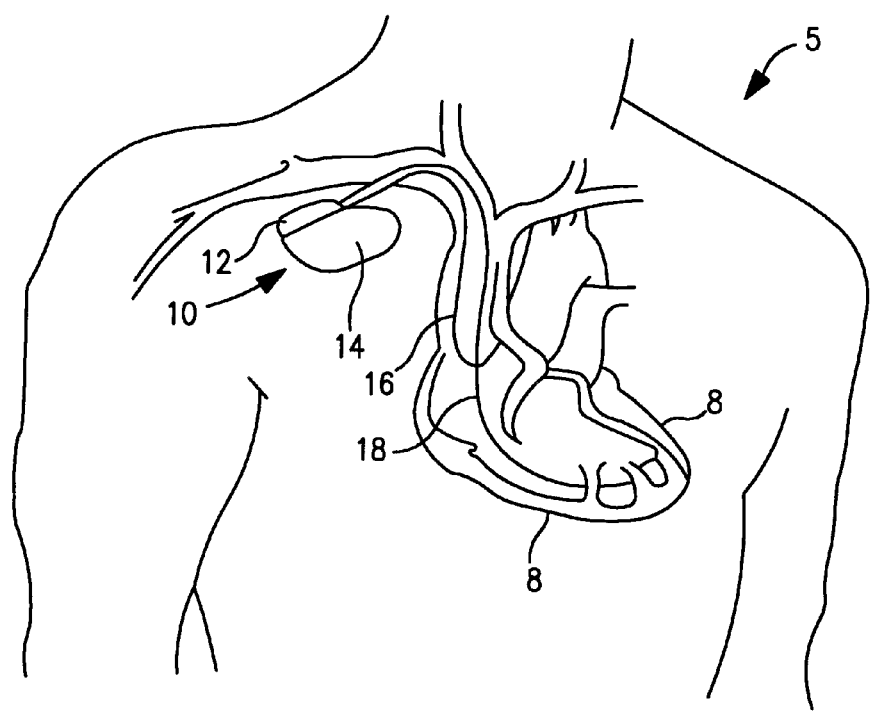
FIG. 1 is a simplified schematic view of one embodiment of an implantable medical device that can be employed in the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
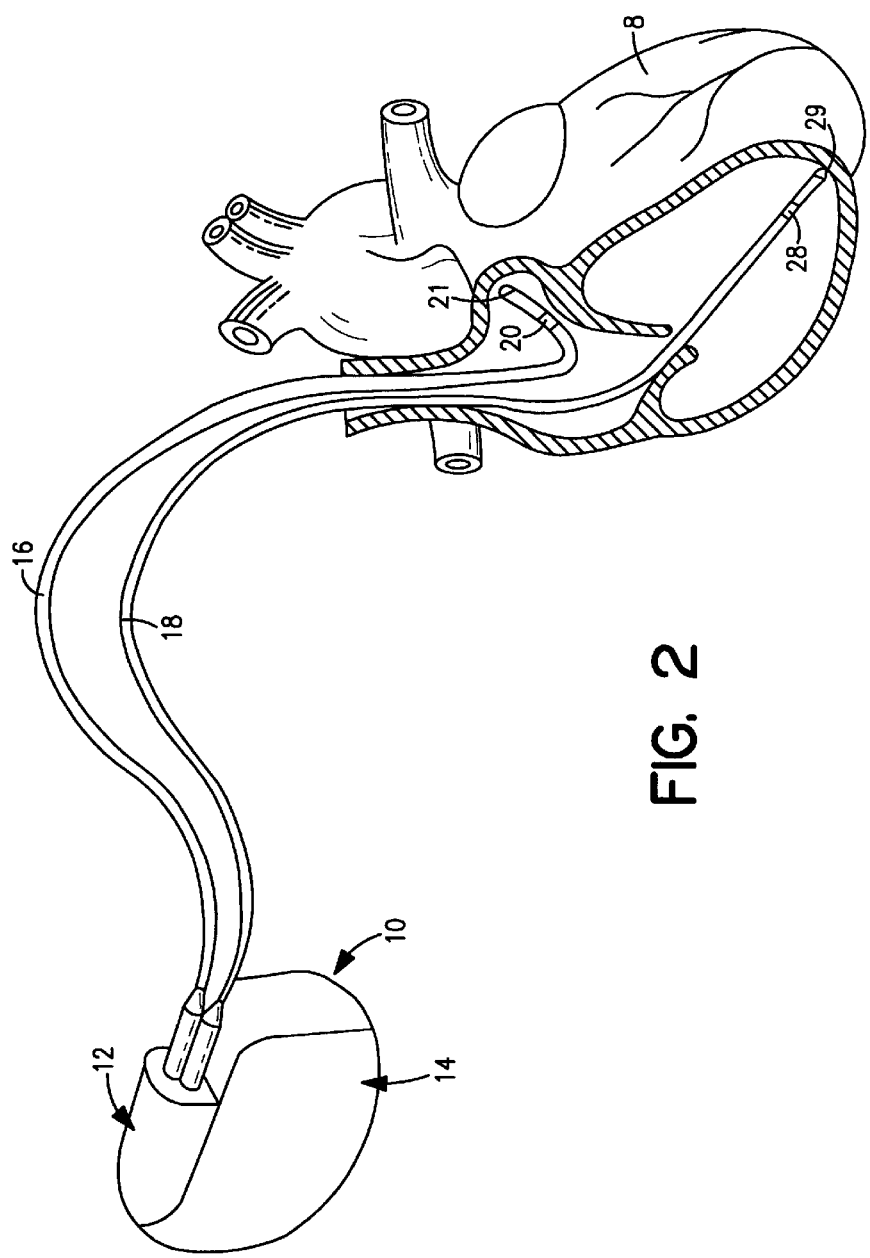
FIG. 2 is a graphic representation of an implantable medical device interconnected with a human or mammalian heart, illustrating the device connector portion and the leads between the device and the heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
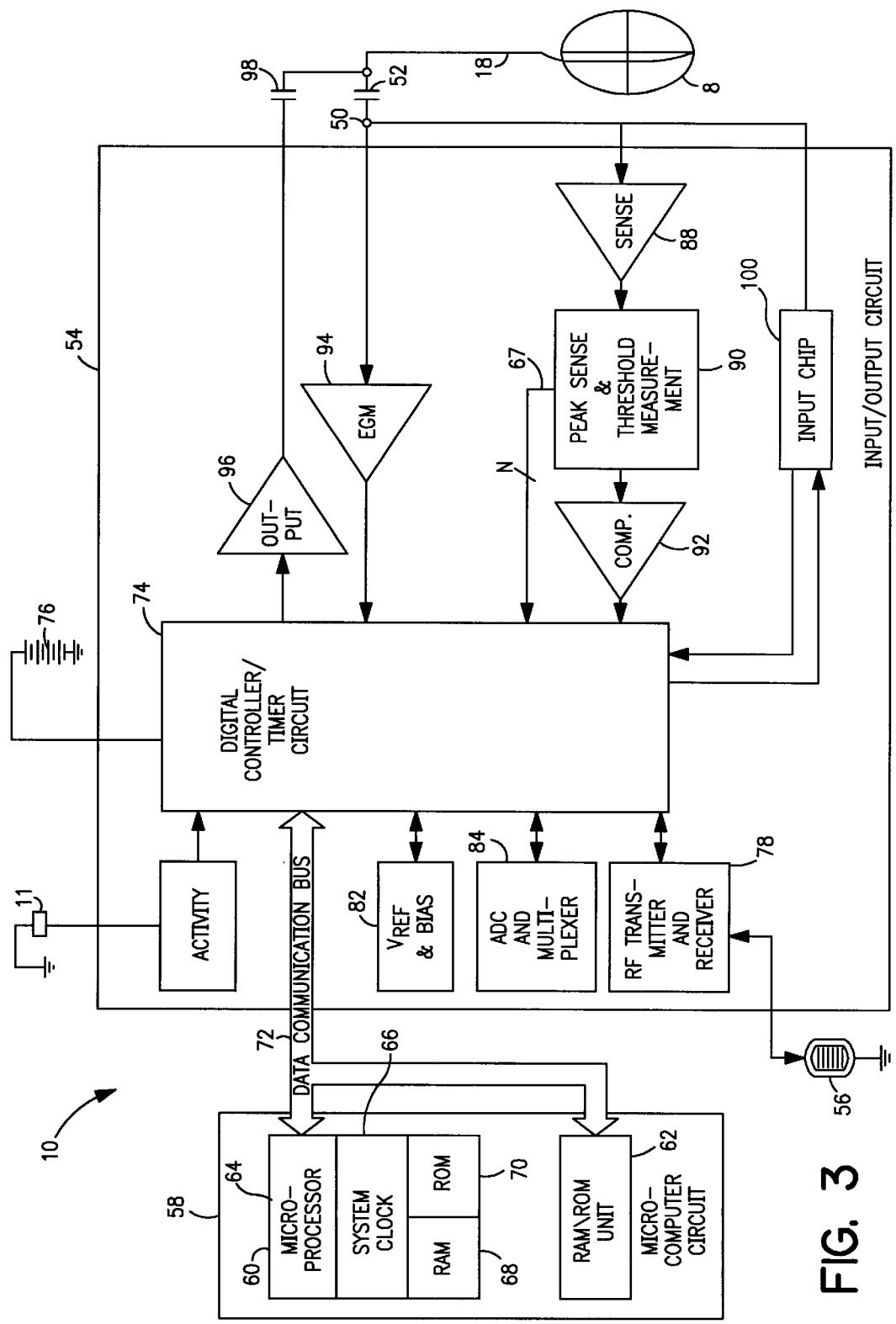
FIG. 3 is a functional schematic diagram showing the primary constituent components of an implantable medical device in accordance with an embodiment of this invention.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry of intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. These circuits may be replaced with an input chip, shown at 100, that incorporates DSP circuitry. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
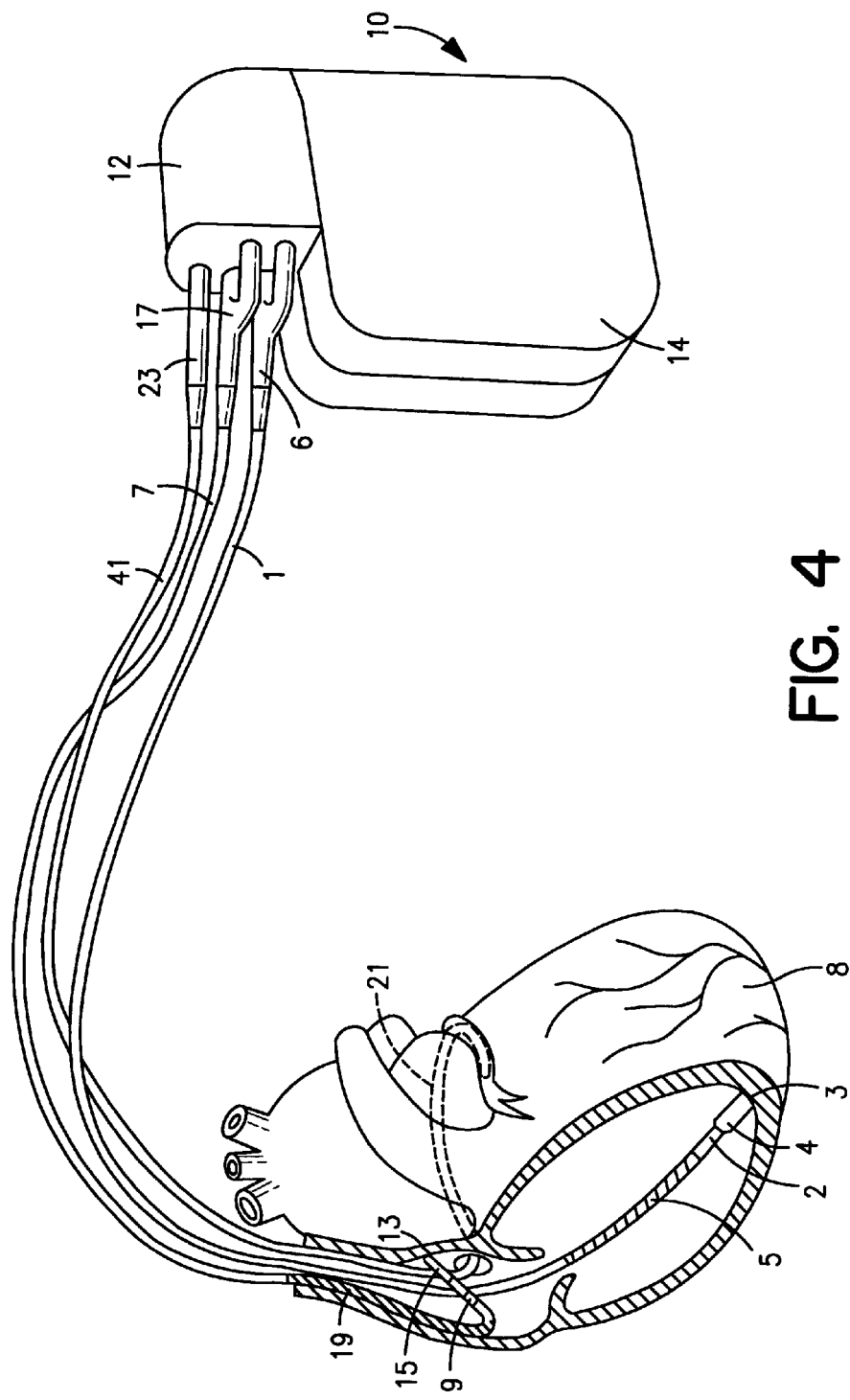
FIG. 4 is a graphic representation of an embodiment of this invention showing an implantable PCD device interconnected with a heart, the system of this embodiment providing pacing, cardioversion and defibrillation.
Figure 5:
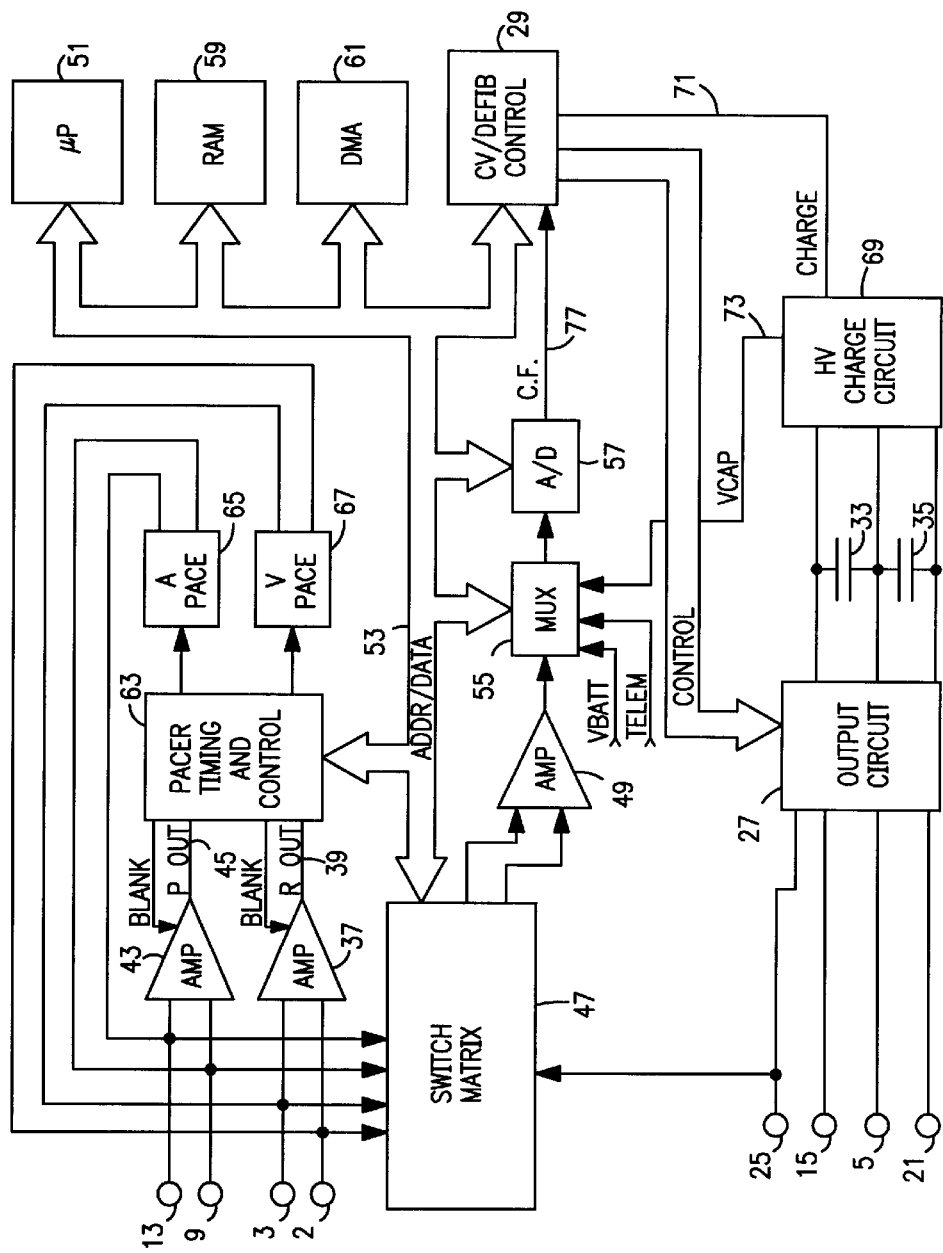
FIG. 5 is a functional schematic diagram of an implantable PCD embodiment of this invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold. For a bi-ventricular pacemaker, electrode 21 of suitable form may be used for unipolar sensing, or together with another electrode placed in the left ventricle for bipolar sensing. Examples of multi-chamber pacemaker systems having lead assemblies for sensing in both left and right ventricles are shown in U.S. Pat. Nos. 5,800,465; 6,070,100; 6,071,101; and 6,219,579, each of which is incorporated herein by reference in its entirety.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The lo suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May-June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14,1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

The system and method of this invention are specifically directed toward providing data regarding the condition of the patient's heart, and particularly toward measuring and storing information from the patient's cardiac signals. Such information is gathered over long periods of time in order to make valid observations of the progression, if any, toward heart failure. The QRST signal is used to obtain the information that is to be processed. QRST signals are obtained from the patient's ventricle, utilizing lead 18, sense amplifier 88 and circuits 90 and 92, as shown in FIG. 3. Alternately, the signals may be transmitted from electrodes 2,3 to R-wave amplifier 37, as depicted in FIG. 5. For sensing in both ventricles, an electrode (or electrodes) is placed in the left ventricle as well, for example, as shown at 21 in FIG. 4, and inputted to a second R wave sensing channel. The entire QRST signal is made up of component portions, or segments, namely the QRS signal, the ST segment between the QRS and T waves, and the T wave. The QT interval is the combination of these segments, each of which is known to vary in a heart that is progressing toward HF. The width of the QRS complex in normal hearts is approximately 130 ms and will become shorter as heart rate increases. Widening of the QRS complex, at all heart rates, but particularly at rest, is a well-known phenomenon in relation to the development of HF. Such QRS widening is caused by depolarization dispersion due to conduction disturbances and increased muscle mass, particularly in end-stage HF.

The ST segment represents the time between the contracted state and the relaxation of the heart muscle. The ST segment in normal hearts is approximately 180 ms and becomes shorter as heart rate increases. The shortening is more pronounced in the ST segment than it is with QRS width. During onset of HF, the heart probably attempts to compensate for the experienced cardiac stress by shortening of the ST segment. At some point, this is no longer possible and the ST segment starts to gradually lengthen. The T wave width is approximately 130 ms in normal hearts, and will become shorter when the heart rate increases and becomes wider at lower heart rates. The T wave represents the relaxation of the heart. Due to depolarization dispersion the T wave will become wider when and as HF progresses.

Table 2, set forth below, indicates changes in QRS width, ST segment length, T wave width, and total QT interval length as anticipated in the various stages of heart failure, where (−) represents a decrease and (+) represents an increase.

TABLE 2

| HF class | QRS width | ST segment | T wave width | Total QT interval |
|---|---|---|---|---|
| I | Normal | − | Normal | − |
| II | + | Normal | + | ++ |
| III | ++ | + | ++ | +++++ |
| IV | +++ | ++ | ++ | +++++++ |

As can be seen, each of the segments of the QRST signal carries information of diagnostic value, as does the overall QRST, or total QT interval length. Although QT interval by itself is the preferred parameter for collection and analysis, in some patients variations in one of the QRST segments by itself may provide more or different information than the QT interval. For this reason, in the practice of this invention one or more of the QRST segments may be utilized in addition to or instead of QT interval. It is to be understood that in the following discussion of the data collection and algorithms utilized in this invention, QT interval or the term QT data is used as embracing any one of or any combination of the QT segments shown in Table 2. Further, the QT interval or other QT data can be obtained from each ventricle.

Figure 6:
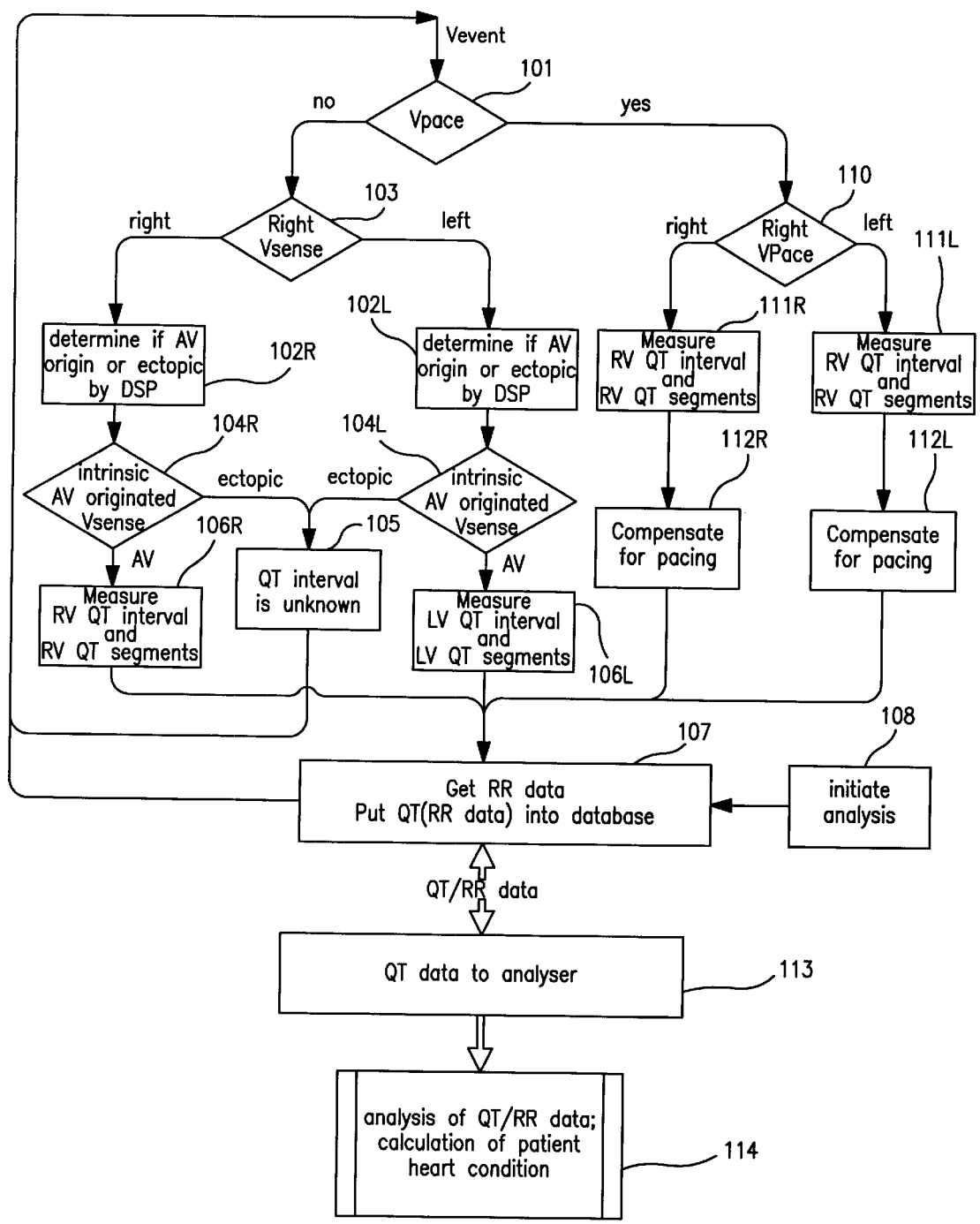
FIG. 6 is an overall flow diagram illustrating the collection of dynamic data for use in indicating degree of heart failure, in accordance with this invention.

FIG. 6 is a flow diagram showing the primary steps of an overall algorithm for collecting, storing and analyzing data in accord with this invention. The algorithm is suitably carried out by a microprocessor subsystem, as described above in connection with FIG. 3 or FIG. 5. FIG. 6 illustrates a bi-ventricular embodiment, but of course the invention can be practiced in relation to just one ventricle. The routine of FIG. 6 may be initiated by the patient or her physician prior to start of exercise, for the collection of dynamic QT parameter data. Alternately, for the collection of QT interval data alone, or the collection of QT segment data, the routine may be initiated automatically, e.g., every week. As indicated at block 101 at the top of the flow diagram, when there is a ventricular event, it is determined whether it is a paced event, i.e., a Vpace. If it is not a Vpace, at 103 it is determined whether the sense signal is a right or left Vsense. If right, then at 102R it is determined if the sense is AV in origin, or ectopic. DSP technology, as shown in U.S. Pat. No. 6,029,087, may be used for handling the signal and for discriminating ectopic beats. If the signal is found to be ectopic at 104R, the algorithm branches to 105, recognizes the signal to be of unknown origin, and no data is recorded. If the beat was AV in origin, then at 106R the QT of the right ventricle is measured, along with the respective QT segments. Returning to 103, if the sense is found to be a left Vsense, then at 102L it is determined if it is ectopic or of AV origin. At 104L, the routine branches to 105 if it has been an ectopic beat, or goes to 106L if it has been a normal AV beat. At 107, the QT and QT segment data found at 106R and 106L is put into a database. The data may be time-stamped each time it is stored in the database, or time may be recorded periodically so that there is a record of the history of the data. Also, for both the left and right senses, the rate, or interval of the most recent V event is stored along with the QT data. The QT and RR data together are referred to as QT/RR data.

If the V event is determined at 101 to be a Vpace, then the flow diagram branches to block 110 and determines whether it has been a left or right pace. If right, the routine branches to 111R and measures the right QT interval and its segments. This data is further processed at 112R to compensate for differences between QT interval when the ventricular signal is evoked by a pacing pulse, and then the algorithm proceeds to 107 to store the new data. Alternately, if at 110 it is found that the pace was in the left ventricle, the routine goes to block 111L and gets the left QT and QT segment data, compensates at 112L for pacing, and stores the data in the data base as shown at 107. Following obtaining and storing of the QT/RR data, the device algorithm generally returns to await the next ventricular event.

Periodically, either on a programmed basis or when initiated by a physician, the device initiates an analysis an indicated at block 108. For example, following exercise and collection of data for calculating dynamic QT parameters, the patient or the physician can initiate analysis. When this is done, the QT/RR data is passed to the analyzer, as shown at block 113. An analysis of the data is performed at 114, resulting in a calculation of patient heart condition. The calculation is suitably adapted as a function of the data obtained, and will vary depending upon whether the analysis is to be based solely upon dynamic data; dynamic data together with QT data; QT data alone; QT segment data; or any combination of the above. The analysis of QT/RR data may be a determination of any one of the dynamic QT parameters discussed below, or any combination of these. This may be done in combination with an analysis of the QT data, or the QT segment data. Also, for a bi-ventricular pacemaker or other implantable cardiac device, the analysis may involve a comparison of left and right data. A simple form of calculation of patient heart condition is calculating change in the dynamic parameter, or parameters, over a predetermined period of time. If the change, or differential is greater than a threshold value, then HF is indicated. A threshold value for each dynamic parameter may be inputted by the physician. Alternately, the calculation may consist of, or include, a comparison of change of QT, QTc, QT segments, or dynamic parameters found in each of the left and right ventricles. Thus, if the change over a period of time in QT or a dynamic QT parameter in the left ventricle exceeds the corresponding change in the right ventricle by a predetermined value, this can represent the onset of HF. A change of QT or a QT parameter by, e.g., more than 10% may be the cause of initiation of a different pacing therapy. Also, the analysis step may include downloading data through a programmer for evaluation by the patient's physician. If the result of the analysis is not to be downloaded, it can be saved with the date of analysis, to provide a historical record. Thus, at some later date, the dynamic QT parameter values can be downloaded along with the dates of calculation, to give an indication of change with time. In this way, a historical record is built.

Figure 7:
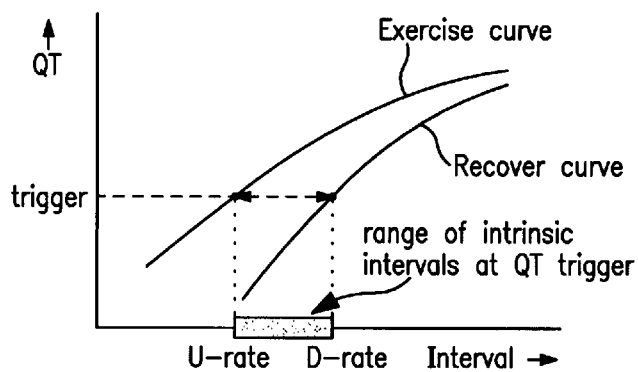
FIG. 7 is a set of curves illustrating the dynamic rate range parameter that is used in this invention.

FIG. 7 shows a first set of QT vs. rate interval curves. A first curve is designated "exercise curve" and a second curve is designated "recover curve". These curves together with the QT interval and rate designations thereon illustrate a first dynamic QT parameter, which we call "dynamic rate range". The exercise curve illustrates that when and as a patient is put into exercise, the rate interval decreases, corresponding to increased heart rate, while the QT interval decreases. A trigger level of QT interval is selected, and when the patient QT drops to the trigger QT value, the pacemaker or implantable device determines the heart rate, designated U-rate. When the patient has safely attained a QT greater than the predetermined trigger value, the patient stops exercise, and the heart recovers back towards rest. As shown, the recover curve is different from the exercise curve. As rate decreases toward rest, and the heart beat interval increases, the time comes when the QT rises back to the trigger level, and at this point the device records the rate corresponding to QT trigger on the recover curve, designated D-rate. As shown in FIG. 7 the difference between U-rate and D-rate is stored as representative of the dynamic rate range of intrinsic heartbeat intervals at QT trigger. Information contained in the dynamic rate range parameter represents not simply a value of QT at a given point, but a dynamic response of the patient's heart to exercise followed by recovery. The information available from this dynamic QT parameter is optimized when the patient is actually taken through the exercise routine. However, the invention also embodies a sequence where the patient heart rate is programmed by the pacemaker to increase heart rate from a lower rest level up to and past the QT trigger level, and then to bring heart rate back down. In this embodiment, the system collects the same dynamic QT parameter data, but without requiring the patient to undergo an exercise sequence. The QT trigger level is programmable, and may be varied in order to collect data over substantially the full range of the QT(RR) curve.

Figure 8:
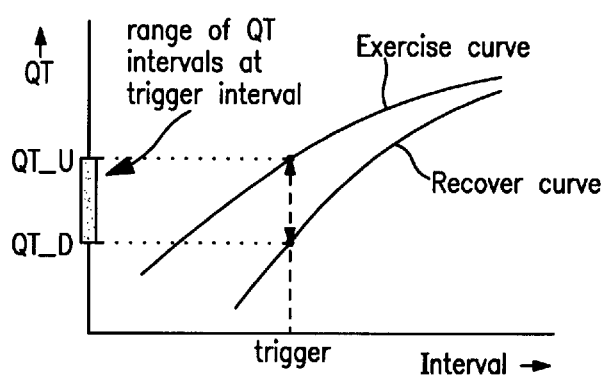
FIG. 8 is a set of curves illustrating the dynamic hysteresis parameter as used in this invention.

FIG. 8 illustrates the method of obtaining a second dynamic QT parameter, namely QT hysteresis. The QT hysteresis parameter is somewhat complementary to the dynamic rate range, comprising determination of differences in QT interval at a given trigger rate. Here, QT is first determined at a predetermined rate trigger when the patient is exercising and heart rate is increasing. Then, QT is again obtained at the same rate trigger when the patient has stopped exercising and heart rate is recovering towards rest. As indicated, the exercise curve and the recover curve are the same as for FIG. 7. In the sequence for obtaining QT hysteresis, the patient starts to exercise and heart beat interval decreases until it reaches the predetermined rate trigger. At this point, the value of QT is measured as QT_U and stored. Exercise is continued until the patient heartbeat interval is safely smaller than the trigger interval, at which point exercise is stopped and the heartbeat commences to return toward rest. Following the recover curve, when rate decreases to the point where the trigger interval is reached, QT is measured as QT_D. The difference between QT_U and QT_D is determined and stored as QT hysteresis.

Figure 9:
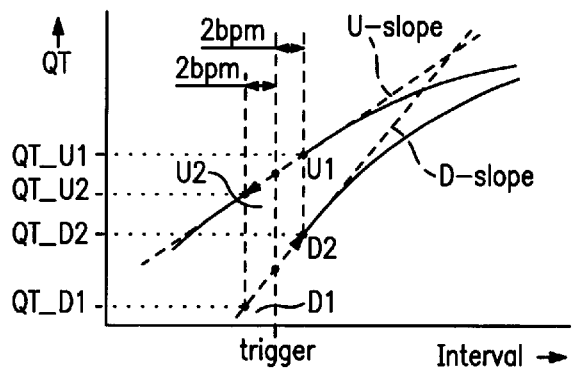
FIG. 9 is a set of curves illustrating the dynamic QT directrix parameter as used in this invention.

FIG. 9 illustrates a third dynamic QT parameter, which we call QT directrix. The concept involved in the QT directrix parameter is that the slope of the QT/RR curve at a given heartbeat rate is different when rate is going up during exercise from what it is when rate is going down during patient recovery. Further, the slopes will change as the patient progresses toward HF, such that the difference in slope over time contains additional information indicative of degree of heart failure. As seen in FIG. 9, the sequence is to have the patient initiate exercise and maintain exercise as the rate rises up through a predetermined rate trigger. As the heartbeat increases through the trigger area, data is obtained from which a calculation of the slope of the QT (RR) curve can be obtained around the trigger rate. This slope is shown by the dashed line designated U-slope. Following increase of the rate higher than the last data point for determining U-slope, exercise is stopped, and the patient heart beat returns towards rest, as shown by the recovery curve. As the heart beat decreases back down through the rate trigger, data points are taken from which a second slope is determined, shown by the dashed line marked D-slope. As shown in FIG. 9, two data points are taken around the trigger level, for each of the slopes. During exercise, QT_U1 is obtained when rate arises to a value designated as U1, which is may be, for example, 2 bpm less than the trigger rate. A second QT value shown as QT_U2 is obtained when rate reaches 2 bpm above the trigger rate. U-slope is then obtained by calculating the QT difference and dividing by the rate difference. Of course, additional data points may be taken to obtain the slope values. After the patient heart rate has increased safely past the U2 level, the patient's stops exercising, and QT values are obtained as the pacing rate drops through D1 and D2, where D1 is likewise 2 bpm above the trigger rate and D2 is 2 bpm below the trigger rate. The down slope is calculated as QT_D2 minus QT_D1 divided by D1 minus D2. Alternately, the area within the Up curve and the Down curve, and bounded by tracing U1 to U2 to D1 to D2 and back to U1 may be calculated, and used as a dynamic parameter indicative of change in heart condition.

While three dynamic parameters are illustrated, it is to be understood that additional such dynamic parameters may be utilized in the practice of this invention. Further, dynamic parameter data may be obtained at more than one trigger value. Thus, dynamic rate range may be obtained at two or more values of QT trigger; and QT hysteresis and directrix may be obtained at two or more rate trigger values. The characteristic of these parameters is that they contain information at rates above the patient's normal rest rate, and thus contain information that is not available from simple QT at rest measurements. The trigger rate may be programmed to different values, in order to obtain data from substantially the entire patient rate range.

Figure 10:
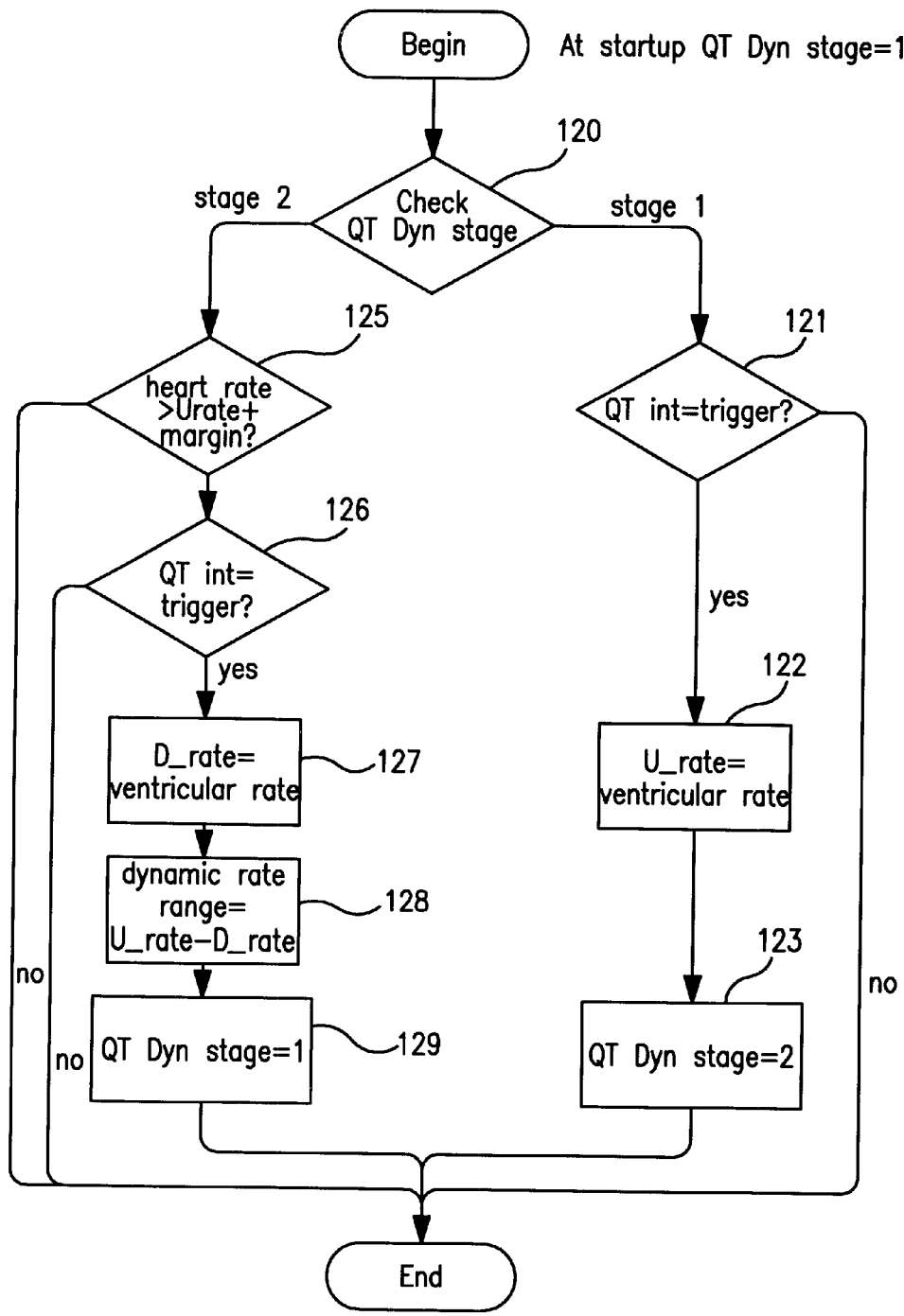
FIG. 10 is a flow diagram illustrating an algorithm for determination of dynamic range data in accordance with the practice of this invention.
Figure 11:
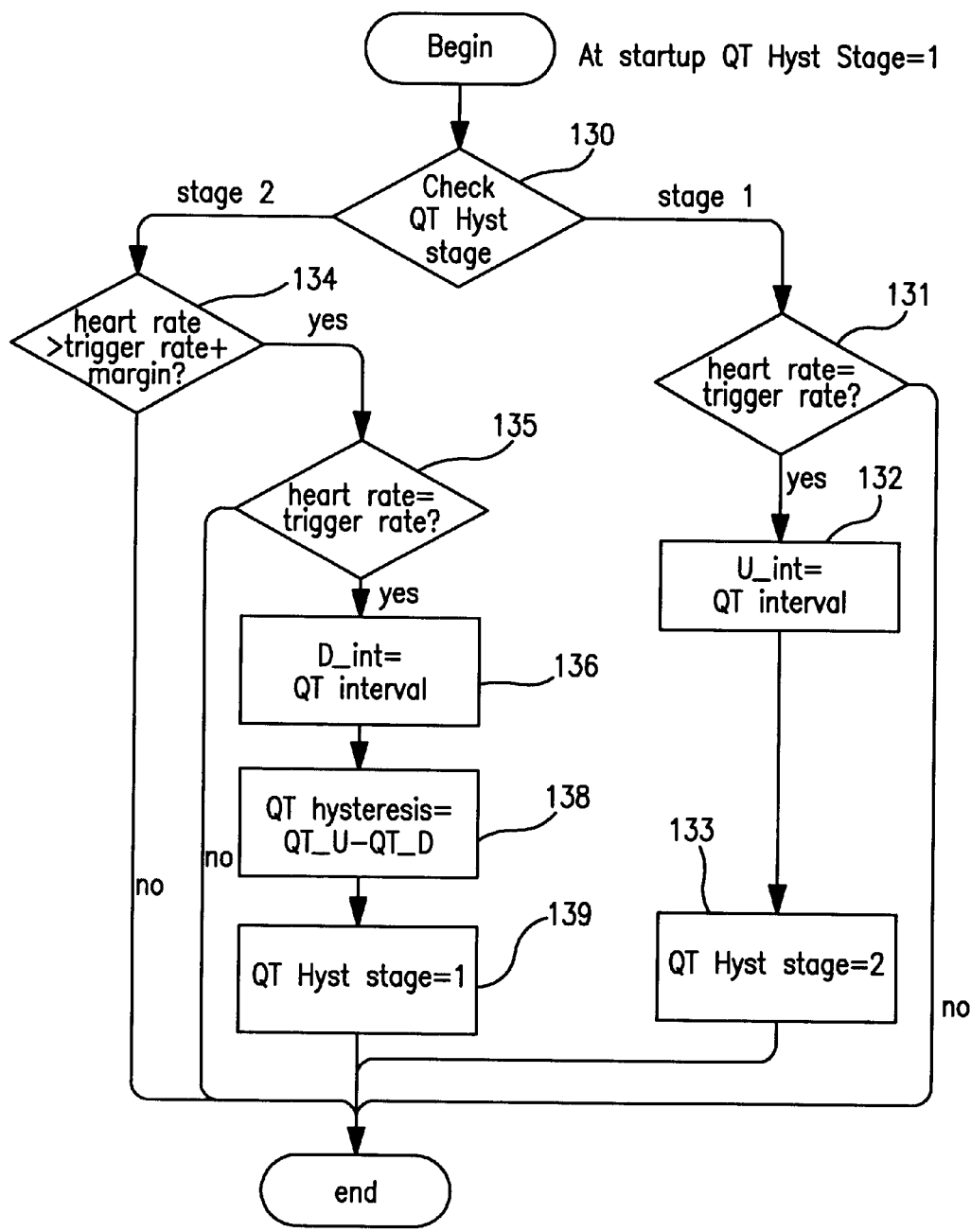
FIG. 11 is a flow diagram illustrating an algorithm for determination of dynamic QT hysteresis data in accordance with the practice of this invention.
Figure 12A:
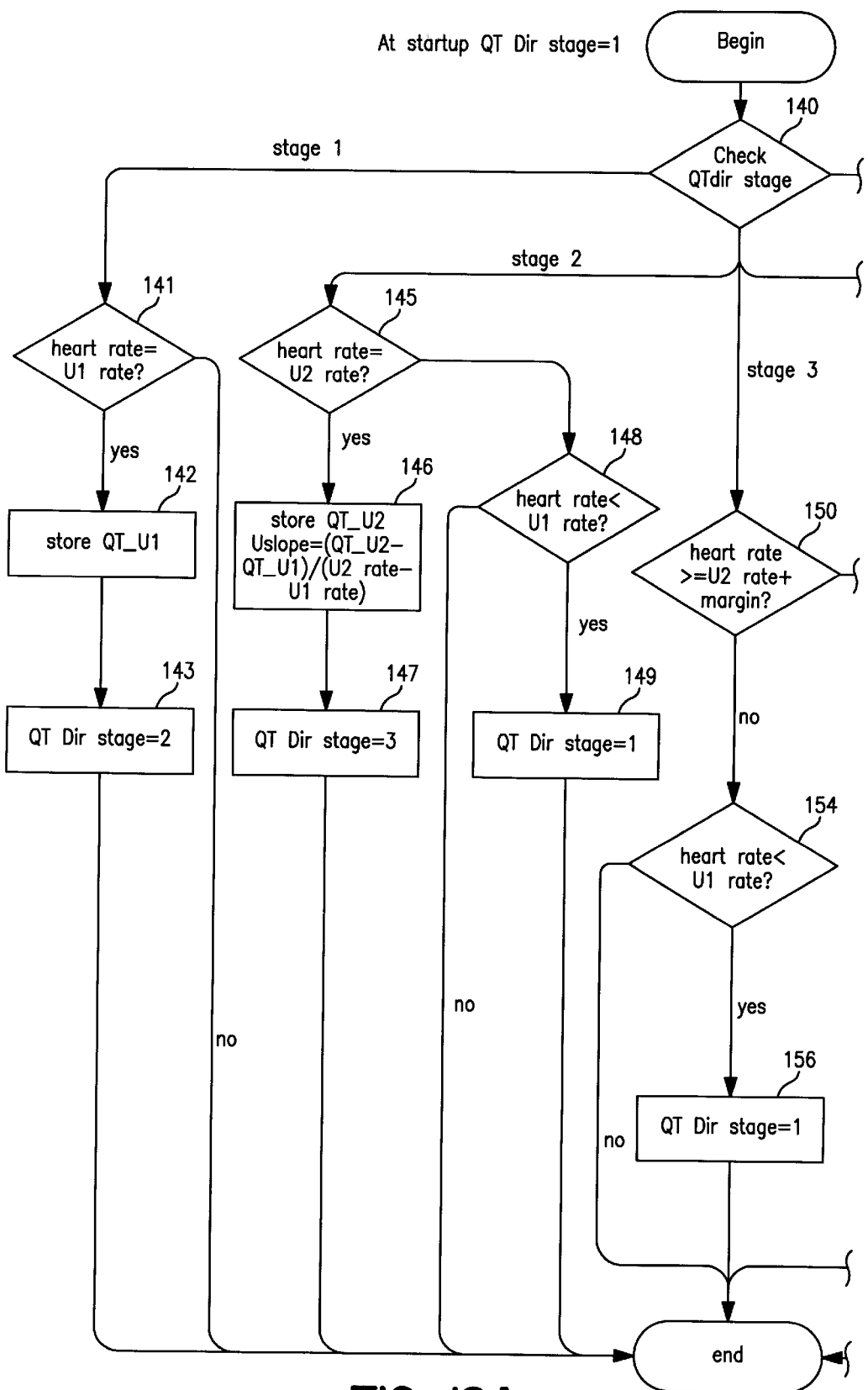
FIG. 12 is a flow diagram illustrating an algorithm for determination of dynamic QT directrix in accordance with the practice of this invention.
Figure 12B:
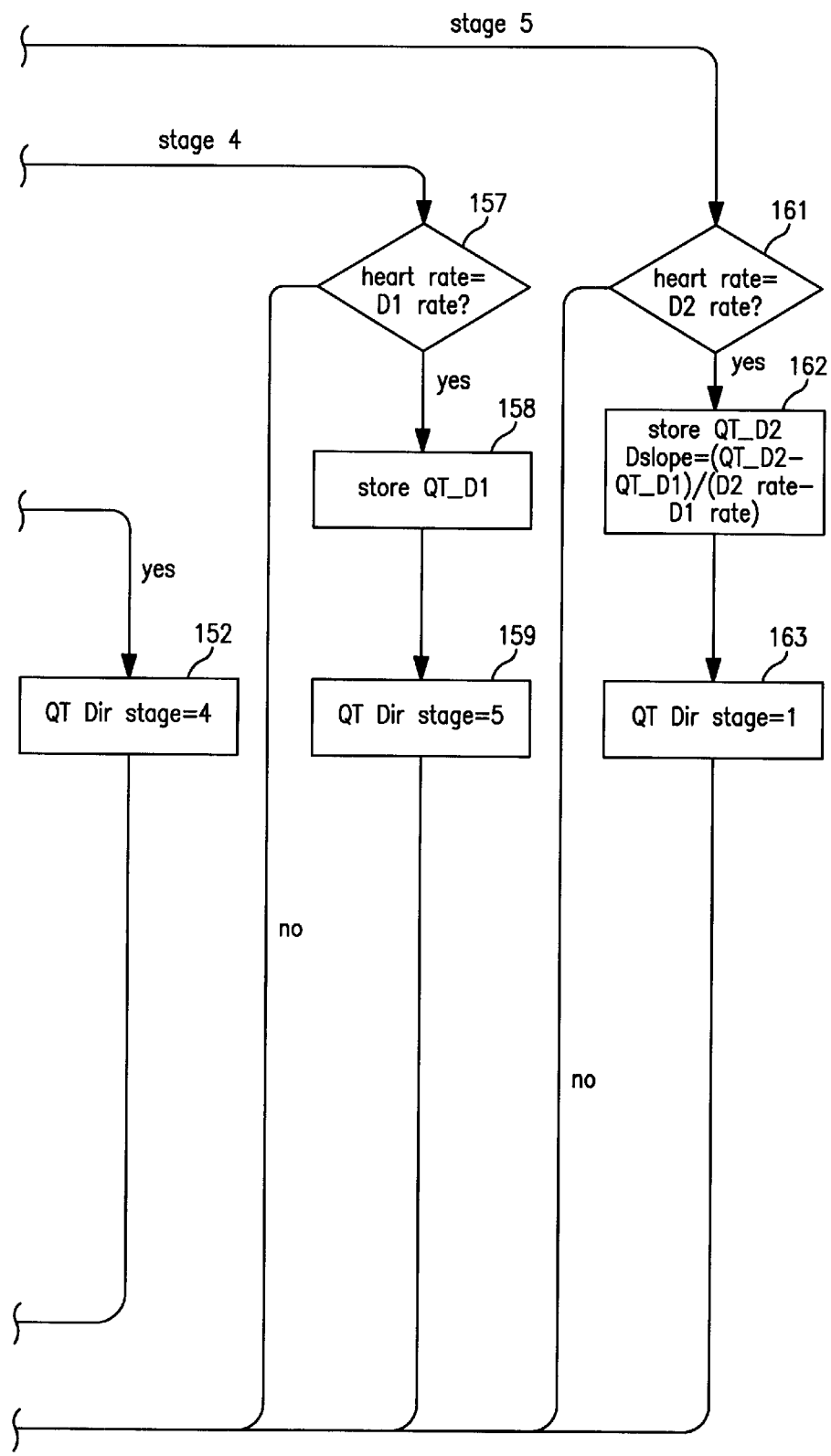

FIG. 10 shows a flow diagram by which an algorithm for determining the dynamic rate range parameter is performed. The steps of FIG. 10, along with the algorithms illustrated in FIGS. 11 and 12 are suitably carried out in a programmed microprocessor, of the type described above in connection with FIGS. 3 and 5. The flow diagram of FIG. 10 corresponds to the steps described in connection with the curves of FIG. 7; the flow diagram of FIG. 11 corresponds to the curves of FIG. 8; and the flow diagram of FIG. 12 corresponds to the curves of FIG. 9.

The algorithm of FIG. 10 is performed when the patient enters the exercise sequence as described above. At start up of the algorithm, a counter or flag "QT DYN stage" is set equal to one. At block 120, the device checks to see whether the algorithm is in stage 1 or stage 2. Assuming that exercise has been initiated, the flag is at stage 1 and the program branches to block 121. It is determined whether QT interval has decreased to the point where it matches the trigger level. If no, the routine branches and begins again at the time of the next sensed heartbeat. When QT becomes equal to the trigger value U-rate (the patient's ventricular rate) is determined. Then, at 123, QT Dyn stage is set equal to 2, and the routine exits back to the beginning. At the occurrence of the next sensed heart beat, at 120 it is determined that the routine is in stage 2, and it branches to block 125 and determines whether the heart rate has increased to a predetermined safety margin above U-rate. If no, the routine starts again at block 120 at the time of the next heartbeat. When it is determined at block 125 that heart rate exceeds U-rate plus margin, and patient exercise has ceased, the heart rate begins to recover along the recover curve. The routine goes to 126 and determines whether QT interval has lengthened back to QT trigger. If no, the routine exits, but if yes it goes to block 127 and determines and stores D-rate, which is the ventricular rate at the trigger QT during recovery following exercise. Then, at 128, the dynamic rate range is calculated as U-rate minus D-rate and stored. QT dynamic stage is returned to value 1 at block 129, and routine exits. Thus, at the conclusion of the exercise routine, in accordance with the method of this invention there has been obtained a value for dynamic rate range that is stored for subsequent use. The dynamic data is suitably stored along with a date, so that it can be accurately analyzed in terms of patient history when it is subsequently compared to one or more other determined values of the dynamic parameter.

FIG. 11 is a flow diagram setting the forth the primary steps taken in a microprocessor or equivalent subsystem, for determining QT hysteresis. A counter or flag referred to as "QT Hyst Stage" is set equal to one at the start of the test. The patient commences exercise, and at each heart beat the routine is entered at 130 by checking QT Hyst Stage. If in Stage 1, the routine branches to block 131 and determines whether the heart rate is equal to the trigger rate. If no, the routine exits. If yes, meaning that exercise has advanced to the point where rate has increased to the trigger rate level, the QT interval is stored as QT_U at 132. At 133 the routine changes QT Hyst Stage to 2 and exits. Following this, the patient continues to exercise until the rate increases above the trigger rate (heart beat interval is below the interval trigger). At 134, if heart rate has not yet exceeded the trigger rate plus a margin, the routine exits. If heart rate has risen above the trigger rate by at least the predetermined margin, the routine goes to 135 and looks to see whether heart rate has come back down to the trigger rate. This will happen after the patient stops exercise, and the heartbeat signal rises along the recover curve shown in FIG. 8. If no, the routine exits, but if yes, at 136 the value of the QT interval, designated QT_D, is recorded. Then, at block 138, QT hysteresis is calculated as QT_U minus QT_D, and stored. As with the other dynamic parameters, the data is suitably stored along with an indication of date, for subsequent historical analysis. Following this, at 139 QT Hyst Stage is set to 1 and the routine exits. As stated above, during any given exercise test, values of QT hysteresis may suitably be obtained at more than one trigger level.

FIG. 12 illustrates a software routine for carrying out the determination of the QT directrix parameter. In this routine, a software counter designated QT Dir Stage is sequenced from 1 through 5, according to advancement through the exercise routine, as seen in following through the logic of the routine. At the beginning point, QT Dir Stage is set equal to 1. Following each sensed heartbeat during the exercise routine, at 140 the Stage is checked. Following the path of Stage 1, at 141 it is determined whether heart rate has reached the value of U1 illustrated in FIG. 9, which is suitably 2 bpm less than the predetermined trigger rate. If no, the routine exits but if yes, at 142 the value of QT is obtained and stored as QT_U1. Then at 143 the stage is set equal to 2.

Returning to 140, when the QT dir stage is set to 2 the routine branches to block 145, and determines whether heart rate has reached U2, illustrated as being 2 bpm higher than the trigger rate. If no, the routine goes to 148 and determines whether the heart rate is less than U1 rate. If yes, the Stage is set back to 1 at 149, and the routine exits. If the answer at 148 is no, the routine exits, and at the next cycle returns to 145. When heart rate is found to have reached U2, at 146 the value of Q2_U2 is stored. The U slope, being the slope of the QT (RR) exercise curve shown in FIG. 9 around the trigger rate, is then calculated according to the formula shown at Block 146 of FIG. 12. Following this, the stage counter is set to 3 at 147, and the routine exits.

When the stage counter is found to be in stage 3 at 140, the routine goes to 150 and determines whether the heart rate has exceeded U2 by a predetermined margin. If heart rate is equal to the U2 rate plus a margin, the routine branches to block 152 and sets the stage to 4. However, if heart rate has not advanced to U2 plus the margin, then at 154 it is determined whether heart rate is below U1. If no, the routine exits, still in stage 3; if yes, the stage is set back to 1 as shown at block 156.

Upon the next sensed heartbeat where the stage is determined to be 4, the routine branches to 157. At this time, the patient has stopped exercise and heart rate will start to decrease. It is determined whether heart rate has dropped down to the D1 rate. If no, the routine exits and recycles back at each next heartbeat. When heart rate is found to be at D1, the routine goes to block 158 and stores the then current value of the QT, being QT_D1. At 159 the stage counter is set equal to 5. As the patient continues to recover from exercise, the heart rate continues to drop, and at each succeeding cycle the routine checks at 161 to determine whether heart rate has dropped to D2. When this is found, at block 162 the value of QT, being QT_D2 is stored. All information required for calculation of the directrix parameter having then been obtained, the directrix value "D slope" is calculated as shown at block 162. The stage is set then back to 1 at 163, and the routine exits. As with the determination of the other dynamic parameters, the directrix value can be determined at a plurality of different rate triggers.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to the 3 dynamic QT parameters illustrated as QT dynamic range, QT hysteresis, and QT directrix. The present invention is also not limited to dynamic QT parameters per se, but may find further application by utilization of different portions of the sensed cardiac signal, including the QT interval and segments of the QRST complex. As stated above, the dynamic parameters and QT data can be determined for each of the left and right ventricle. The present invention further includes within its scope methods of making and using the diagnostic algorithms described here and above.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. An implantable medical device system, having lead means for receiving intracardiac signals from a patient's heart, sensing means for sensing QRS-T signals from said received signals, and indicator means for obtaining indications of the degree of patient heart failure, said indicator means comprising:

rate means for determining patient heart rate values from said received signals, and for storing said heart rate values;

QT means for obtaining from said sensed signals values of QT, and for storing respective QT values corresponding to said determined patient heart rate values;

dynamic means for generating from said stored QT values and heart rate values dynamic data representative of changes of QT and heart rate; and analysis means for analyzing said dynamic data and determining therefrom an indication of degree of patient heart failure;

wherein said dynamic means comprises a range rate algorithm for determining dynamic range rate data, said range rate algorithm comprises means for determining at least one QT trigger level, and rate difference means for determining the difference between (a) the patient heart rate when exercising and QT shortens to said QT trigger level, and (b) the patient heart rate after cessation of exercise and QT lengthens back to said QT trigger level.

2. The system as described in claim 1, wherein said system comprises an implantable pacing device, said pacing device having a generator for generating pacing pulses, said lead means has leads for delivering said pacing pulses to the patient's heart, and said pacing device has a microcomputer circuit programmed for use in generating and analyzing of said dynamic data.

3. An implantable cardiac system, having means for sensing QRST signals from a patient's left and right ventricles and indicator means for obtaining an indication of the degree of heart failure of said patient, said indicator means comprising:

QT means for obtaining from said sensed QRST signals QT values, and for storing said QT values;

segment means for obtaining from said QRST signals data representative of respective segments of each QRST signal and for storing said segment data together with said QT values;

program means for programming said QT means and said segment means to operate according to a predetermined program so as to obtain and store data at different times, thereby providing historical data; and analysis means for analyzing said historical data by comparing QT values and segment data from the patient's left ventricle with QT values and segment data from the patient's right ventricle and providing from such analysis an indication of the degree of heart failure of said patient.

4. The system as described in claim 3, wherein said segment means comprises means for determining from each said QRST signal a value of the QRS width.

5. The system as described in claim 3, wherein said segment means comprises means for determining from each said QRST signal a value of the T wave width.

6. The system as described in claim 1, further comprising QT rest means for obtaining from said QRS-T signals and heart rate values data representative of variation of patient QT values at rest, and where said analyzing means comprises means for determining degree of heart failure as a function of said QT at rest data and said dynamic data.

7. The system as described in claim 1, further comprising QT segment means, and wherein said analyzing means comprises means for determining degree of heart failure as a function of variation in at least one segment of said QRT-T signal.

8. The system as described in claim 3, wherein said segment means comprises means for determining from each said QRST signal a value of ST segment.

9. The system as described in claim 8, wherein said dynamic means comprises a QT hysteresis algorithm for determining QT hysteresis data.

10. The system as described in claim 9, wherein said QT hysteresis algorithm comprises means for determining at least one heart rate trigger value, and QT difference means for determining the difference between (a) the QT when exercising and rate shortens to said trigger value, and (b) the QT after cessation of exercise and rate increases back to said trigger value.

11. The system as described in claim 8, wherein said dynamic means comprises a QT directrix algorthim for determining dynamic QT directrix data.

12. The system as described in claim 3, comprising rate means for obtaining values of patient heart rate corresponding to each said QRST signal, dynamic means for generating from said QT values and said rate values dynamic data representative of changes of QT and heart rate and for storing said dynamic data, and wherein said analysis means comprises means for providing said indication as a function of said dynamic data.

13. The system as described in claim 3, comprising rate means for obtaining values of patient heart rate corresponding to each said QRST signal, dynamic means for generating from said segment data and said rate values dynamic data representative of changes of at least one of said segments and heart rate and for storing said dynamic data, and wherein said analysis means comprises means for providing said indication as a function of said dynamic data.

14. The system as described in claim 3, comprising bi-ventricular means for obtaining QRST signals from both of the patient's ventricles, and wherein said indicator means has comparison means for comparing said QRST signals from each ventricle.

15. A method of providing an indication of degree of heart failure of a patient, said patient having an implanted medical device system having the capability of sensing and storing patient cardiac signals and of processing the sensed signals, the method utilizing said system and comprising:

sensing cardiac signals and determining patient heart rate values from said sensed signals, and storing said heart rate values;

obtaining values of QT from said sensed signals and storing respective QT values corresponding to said heart rate values;

generating from said stored QT values and heart rate values dynamic data representative of changes of QT and heart rate with patient history;

analyzing said dynamic data in accord with a predetermined algorithm to determine an indication of the patient's degree of heart failure;

having the patient exercise in order to raise the patient's heart rate, and executing first portions of said determining and obtaining while patient heart rate is rising in response to exercise; and having the patient stop exercise to allow patient heart rate to recover down, and executing second portions of said determining and obtaining while patient heart rate is dropping.

16. The method as described in claim 15, comprising generating and storing dynamic QT hysteresis data.

17. The method as described in claim 15, comprising generating and storing dynamic rate range data.

18. The method as described in claim 15, comprising generating and storing dynamic QT directrix data.

19. The method as described in claim 15, comprising sensing cardiac signals from the patient's right ventricle.

20. The method as described in claim 15, comprising sensing cardiac signals from the patient's left ventricle.

21. The method as described in claim 15, comprising performing said determining around a predetermined trigger point on the patient's QT(RR) curve, and programming said trigger point.

22. The method as described in claim 15, wherein said device system has a pacemaker, and comprising pacing said patient at increasing rates and executing first portions of said determining and obtaining, and then pacing said patient at decreasing rates and executing second portions of said determining and obtaining.

23. The method as described in claim 15, comprising sensing cardiac signals from the patient's left ventricle.

24. A method of obtaining data indicative of a patient's heart failure status, said method utilizing a multi-chamber pacing system that can receive signals from each of the patient's ventricles, comprising:

receiving signals from each of the patient's left and right ventricles;

determining heart rate values and measures of QT from said signals for each ventricle and storing sets of said heart rate values and QT measures as QT/RR data;

providing historical data representative of the variation of said QT/RR data for said left and right ventricles; and, comparing variations of QT interval in the two ventricles at at least one programmable heart rate.

25. The method as described in claim 24, comprising determining dynamic QT data, and comparing variations of said QT data in the two ventricles.

26. The method as described in claim 24, comprising initiating analysis of said QT/RR data from an external programmer.

27. The method as described in claim 24, comprising automatically initiating analysis of said QT/RR data by said pacing system.

28. The method as described in claim 24, comprising storing historical time data with at least some of said stored sets of QT/RR data.

29. The method as described in claim 24, comprising downloading said QT/RR data for review by a physician.

30. An implantable medical device system adapted for obtaining data concerning the cardiac condition of a patient, said system having a device and a lead system interconnecting said device with the patient's left and right ventricles for providing QRST signals from both ventricles comprising:

a signal input to which patient cardiac signals can be delivered; sensing circuitry adapted to sense delivered cardiac signals; rate means for determining heart rate values from said cardiac signals;

QT means for obtaining values of QT from said cardiac signals and storing said QT values;

dynamic QT parameter means for episodically generating and storing dynamic QT parameter data from said stored heart rate values and QT values;

output means for outputting said QT parameter data for review; and, means for comparing QT parameter from the patient's left ventricle with QT parameter data from the patient's right ventricle.

31. The system as described in claim 30, wherein said device comprises a programmable processor having an algorithm for analyzing said dynamic QT data taken from a plurality of episodes and determining a measure of patient heart condition from said analyzing.

32. The system as described in claim 30, comprising means for storing historical time data with said stored QT parameter data.

33. The system as described in claim 30, wherein said lead system comprises a lead for interconnecting said device with the patient's right ventricle for providing QRST signals from the right ventricle.

34. The system as described in claim 30, wherein said lead system comprises a lead for interconnecting said device with the patient's left ventricle for providing QRST signals from the left ventricle.

35. A method of collecting data representative of change in a patient's heart condition, said method utilizing an implantable cardiac device system adapted to receive signals from at least one of the patient's ventricles, comprising:

periodically obtaining QT and rate data from said signals;

storing said QT and rate data in a historical database;

comparing said data in said database to determine differences as a function of time;

calculating a plurality of respective dynamic QT parameters and storing them; and, programming trigger rates around which to calculate said dynamic parameters, said rates being within the patients pacing rate range.

36. The method as described in claim 35, comprising calculating at least one dynamic QT parameter and storing said calculated parameter.

37. The method as described in claim 35, comprising downloading said data to an external device, whereby said data can be analyzed by a physician.

38. The method as described in claim 35, comprising performing said obtaining and storing stops while the patient first exercises and then recovers after exercise.

39. The method as described in claim 38, comprising downloading said stored data to an external device, and performing said comparing step external to the patient.

40. The method as described in claim 35, comprising obtaining said data from the patient's right and left ventricles.

41. The method as described in claim 35, comprising initiating the steps of obtaining and storing data when the patient is exercising.

42. The method as described in claim 41, comprising having the patient stop exercising, and obtaining and storing additional such QT and rate data while the patient is recovering from exercise.

* * * * *